(12) United States Patent
Yang et al.

(10) Patent No.: US 9,248,147 B2
(45) Date of Patent: *Feb. 2, 2016

(54) METHODS FOR ENDOSCOPIC MUCOSAL RESECTION AND ENDOSCOPIC SUBMUCOSAL DISSECTION

(71) Applicant: Board Of Regents, The University of Texas System, Austin, TX (US)

(72) Inventors: Jian Yang, University Park, PA (US); Minh-Tuan Richard Tran, Fort Worth, TX (US); Michael W Palmer, Arlington, TX (US); Shou-Jiang Tang, Ridgeland, MS (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/084,935

(22) Filed: Nov. 20, 2013

(65) Prior Publication Data

US 2014/0086866 A1    Mar. 27, 2014

Related U.S. Application Data

(63) Continuation of application No. 13/425,750, filed on Mar. 21, 2012, now Pat. No. 8,613,944.

(60) Provisional application No. 61/454,766, filed on Mar. 21, 2011.

(51) Int. Cl.
| | | |
|---|---|---|
| *A61P 41/00* | (2006.01) |
| *A61K 31/745* | (2006.01) |
| *A61F 2/02* | (2006.01) |
| *A61K 31/765* | (2006.01) |
| *G01N 33/50* | (2006.01) |

(52) U.S. Cl.
CPC .......... *A61K 31/765* (2013.01); *G01N 33/5088* (2013.01)

(58) Field of Classification Search
None
See application file for complete search history.

(56) References Cited

U.S. PATENT DOCUMENTS

| | | | |
|---|---|---|---|
| 6,486,232 B1 * | 11/2002 | Wise et al. ............... | 523/118 |
| 2009/0157114 A1 * | 6/2009 | Fischer et al. ............ | 606/192 |
| 2011/0124765 A1 * | 5/2011 | Yang et al. ............... | 522/87 |
| 2011/0293699 A1 * | 12/2011 | Bennett et al. ........... | 424/450 |

FOREIGN PATENT DOCUMENTS

WO    WO 2009137715 A2 *  11/2009

* cited by examiner

*Primary Examiner* — H. Sarah Park
(74) *Attorney, Agent, or Firm* — John P. Zimmer; Smith Moore Leatherwood LLP (57) ABSTRACT

In one aspect, methods for separating biological tissue are described herein. In some embodiments, a method for separating tissue comprises providing a first composition comprising a polymerizable material, providing a second composition comprising a polymerization initiator, disposing the first composition at a first site beneath a first tissue layer, disposing the second composition at the first site, polymerizing the polymerizable material at the first site, and separating the first tissue layer from a second tissue layer.

19 Claims, 7 Drawing Sheets

METHODS FOR ENDOSCOPIC MUCOSAL RESECTION AND ENDOSCOPIC SUBMUCOSAL DISSECTION

CROSS REFERENCE TO RELATED APPLICATIONS

This application is a continuation of application Ser. No. 13/425,750 filed Mar. 21, 2012, which claims priority pursuant to 35 U.S.C. §119(e) to U.S. Provisional Patent Application Ser. No. 61/454,766, filed on Mar. 21, 2011, which is hereby incorporated by reference in its entirety.

STATEMENT REGARDING FEDERALLY SPONSORED RESEARCH

This invention was made with government support under CAREER award contract 0954109 awarded by the National Science Foundation (NSF), R21 award contract EB009795 awarded by the National Institute of Biomedical Imaging and Bioengineering (NIBIB), and R01 award contract 1R01EB012575-01A1 awarded by the NIBIB. The government has certain rights in the invention.

FIELD

This invention relates to compositions, systems, and methods for separating tissue, and, in particular, to endoscopic mucosal resection (EMR) and endoscopic submucosal dissection (ESD).

BACKGROUND

Gastrointestinal (GI) cancers account for many new cases of cancer reported each year. It is estimated that over 25% of all cancers are GI related, with a majority of these occurring in the stomach and colon. Endoscopic mucosal resection (EMR) and endoscopic submucosal dissection (ESD) are acknowledged as minimally invasive methods of removing dysplasias and early cancers confined to the mucosal or submucosal layers of the GI tract. However, EMR and ESD have been associated with complications due to coincidental damage to underlying muscle layers, such as perforation and hemorrhaging.

To reduce these risks, a solution can be injected beneath the site of interest to physically separate diseased tissue from the underlying muscalaris propria before resection. However, prior injection materials for endoscopic resection are limited by small mucosal lift heights, short mucosal lift durations, high costs, complex preparatory requirements, administration difficulties, and/or localized tissue inflammation.

SUMMARY

In one aspect, methods for separating biological tissue are described herein. In some embodiments, a method for separating tissue comprises providing a first composition comprising a polymerizable material, providing a second composition comprising a polymerization initiator, disposing the first composition at a first site beneath a first tissue layer, disposing the second composition at the first site, polymerizing the polymerizable material at the first site, and separating the first tissue layer from a second tissue layer. In some embodiments, polymerizing the polymerizable material comprises cross linking the polymerizable material. In some embodiments, polymerizing the polymerizable material comprises forming a gel. Moreover, in some embodiments, the separation of the first and second tissue layers is at least partially caused by the polymerization of the polymerizable material at the first site.

Further, separating the first and second tissue layers, in some embodiments, comprises providing a gas between the first and second tissue layers. In some embodiments, the separation of the first and second tissue layers is at least partially caused by the presence of the gas.

In addition, in some embodiments, a method described herein further comprises maintaining separation of the first and second tissue layers for a therapeutically effective period of time. Further, in some embodiments, a method described herein further comprises removing at least a portion of the first tissue layer from the body.

In some embodiments, a method described herein further comprises degrading a polymerizable material and/or a polymerization product of the polymerizable material. Degrading, in some embodiments, comprises biodegrading.

In some embodiments, a method described herein further comprises dispensing a drug into a tissue layer from a composition or gel described herein. In some embodiments, a method described herein further comprises dispensing an imaging agent into a tissue layer from a composition or gel described herein.

In another aspect, systems for use in tissue separation applications are described herein. Tissue separation applications, in some embodiments, include endoscopic resection applications such as EMR and ESD, including injection-assisted EMR and ESD. In some embodiments, a system for use in tissue separation applications comprises a first composition comprising a polymerizable material, a second composition comprising a polymerization initiator, and an endoscopic device. The second composition, in some embodiments, further comprises a gas foaming agent.

In another aspect, methods for displacing soft biological tissue are described herein. In some embodiments, a method for displacing soft tissue comprises providing a first composition comprising a polymerizable material, providing a second composition comprising a polymerization initiator, disposing the first composition at a first site within a first soft tissue, disposing the second composition at the first site, polymerizing the polymerizable material at the first site, and displacing the first soft tissue.

In another aspect, systems for use in tissue displacement applications are described herein. Tissue displacement applications, in some embodiments, include cosmetics applications such as anti-wrinkle applications and lip-plumping applications. In some embodiments, a system for use in tissue displacement applications comprises a first composition comprising a polymerizable material, a second composition comprising a polymerization initiator, and an injection device.

These and other embodiments are described in greater detail in the detailed description which follows.

DETAILED DESCRIPTION

Embodiments described herein can be understood more readily by reference to the following detailed description, examples, and drawings. Elements, apparatus, and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

I. Methods for Separating Tissue

In one aspect, methods for separating biological tissue are described herein. In some embodiments, a method for separating tissue comprises providing a first composition comprising a polymerizable material, providing a second composition comprising a polymerization initiator, disposing the first composition at a first site beneath a first tissue layer, and disposing the second composition at the first site. The first site, in some embodiments, comprises an interfacial region between a first tissue layer and a second tissue layer, including an interfacial region between two differing tissue types. Moreover, in some embodiments, the first composition further comprises a cross linker. In some embodiments, the second composition further comprises a gas foaming agent. In some embodiments, the first composition and/or the second composition further comprises a drug and/or an imaging agent.

In addition, a method described herein further comprises polymerizing the polymerizable material at the first site. Moreover, in some embodiments, polymerization occurs only or primarily at the first site. Polymerizing the polymerizable material at the first site, in some embodiments, permits additional control of the time and place of tissue separation. Further, in some embodiments, polymerizing the polymerizable material after disposing the material beneath a first tissue layer can avoid undesirable events, such as clogging of an endoscopic needle prior to disposition of the polymerizable material beneath the first tissue layer.

In addition, in some embodiments, the polymerization of a polymerizable material described herein is initiated by combining the first composition with the second composition. In particular, in some embodiments, polymerization is initiated by combining a polymerizable material of the first composition with a polymerization initiator of the second composition.

Further, in some embodiments described herein, polymerizing a polymerizable material comprises cross linking the polymerizable material. Cross linking, in some embodiments, is facilitated by a cross linker of the first composition. A cross linker, in some embodiments, is operable to cross link a polymerizable material to provide a polymer network. In other embodiments, a polymerizable material can undergo cross linking without the need for an additional cross linker.

In some embodiments, polymerizing a polymerizable material comprises forming a gel. A gel, in some embodiments, comprises a continuous phase formed from a cross linked polymerizable material. In other embodiments, a gel comprises a discontinuous phase formed from a cross linked polymerizable material. In some embodiments, a gel comprises a hydrogel. A hydrogel, in some embodiments, comprises an aqueous continuous phase and a polymeric disperse or discontinuous phase.

Further, in some embodiments, polymerizing a polymerizable material does not comprise photo-polymerizing or thermo-polymerizing the material. Therefore, in some embodiments, polymerizing a polymerizable material does not require the use of additional equipment, such as an ultraviolet (UV) light source.

A gel comprising a cross linked polymerizable material described herein, in some embodiments, exhibits desirable biological, mechanical, and/or electrical properties. For instance, in some embodiments, a gel described herein is biodegradable. A biodegradable gel, in some embodiments, degrades in vivo to non-toxic components which can be cleared from the body by ordinary biological processes. In some embodiments, a biodegradable gel described herein completely or substantially completely degrades in vivo over the course of about 4 weeks or less. Further, in some embodiments, a gel described herein is biocompatible or cytocompatible. A biocompatible or cytocompatible gel, in some embodiments, is non-toxic and does not cause substantial tissue inflammation.

Moreover, the biodegradability and/or biocompatiblity of a gel described herein, in some embodiments, can be tuned by altering one or more of the components of a first and/or second composition described herein. For example, in some embodiments, the biodegradability or biocompatibility of a gel can be altered based on the identity and/or amount of one or more of a polymerizable material, cross linker, and polymerization initiator described herein.

Further, in some embodiments, a gel described herein is a strong but soft gel. In some embodiments, for instance, a gel described herein is elastomeric. In some embodiments, a gel described herein has a high compressive peak stress and a low initial modulus. For example, in some embodiments, a gel has a compressive peak stress of up to about 20 kPa when measured as described hereinbelow. In some embodiments, a gel has a compressive peak stress of up to about 10 kPa. In some embodiments, a gel has a compressive peak stress between about 0.5 kPa and about 20 kPa, between about 1 kPa and about 15 kPa, between about 3 kPa and about 12 kPa, or between about 5 kPa and about 10 kPa when measured as described hereinbelow. Moreover, in some embodiments, a gel has an initial modulus of up to about 10 kPa. When measured as described hereinbelow. In some embodiments, a gel has an initial modulus of up to about 5 kPa. In some embodiments, a gel has an initial modulus between about 0.5 kPa and about 10 kPa, between about 1 kPa and about 9 kPa, between about 1 kPa and about 5 kPa, or between about 3 kPa and about 5 kPa when measured as described hereinbelow.

In addition, in some embodiments, the mechanical properties of a gel described herein can be tuned by altering one or more of the components of a first and/or second composition described herein. For example, in some embodiments, the mechanical properties can be altered based on the identity and/or amount of one or more of a polymerizable material, cross linker, and polymerization initiator described herein. Therefore, the strength and softness of a gel described herein, in some embodiments, can be tuned to fit a specific application.

Moreover, in some embodiments, a gel described herein has a high electrical resistance. A high electrical resistance, in some embodiments, improves the performance of electrosurgery, such as electrocautery of diseased tissue, by increasing impedance and/or heat dissipation. Further, in some embodiments, the electrical properties of a gel described herein can be tuned by altering one or more of the components of a first and/or second composition described herein. For example, in some embodiments, the electrical properties can be altered based on the identity and/or amount of one or more of a polymerizable material, cross linker, and polymerization initiator described herein.

In addition, in some embodiments, a gel described herein has a tunable gel point or gel setting time. A gel point or gel setting time, in some embodiments, corresponds to the crossover of viscous and elastic moduli of the gel in rheology measurements carried out as described herein. In some embodiments, a gel described herein has a short gel point or gel setting time. Rapid gel setting, in some embodiments, permits more rapid tissue separation and/or resection procedures, such as endoscopic resection procedures. In other embodiments, a gel has a long gel point or gel setting time. Less rapid gel setting, in some embodiments, can facilitate additional or longer procedures, such as additional preparation and/or treatment procedures. In some embodiments, a gel has a gel setting time of less than about 10 minutes. In some embodiments, a gel has a gel setting time of less than about 5 minutes or less than about 4 minutes. In some embodiments, a gel has a gel setting time between about 1 minute and about 30 minutes, between about 1 minute and about 10 minutes, or between about 1 minute and about 5 minutes.

Moreover, the gel point or gel setting time of a gel described herein, in some embodiments, can be tuned by altering one or more of the components of a first and/or second composition described herein. For example, in some embodiments, the gel point or gel setting time can be altered based on the identity and/or amount of one or more of a polymerizable material, cross linker, and polymerization initiator described herein.

In addition, in some embodiments described herein, forming a gel comprises expanding the total volume of a material, such as a combination of first and second compositions described herein. In some embodiments, forming a gel comprises expanding a total volume by up to about 200%. In some embodiments, forming a gel comprises expanding a total volume by up to about 100%. In some embodiments, a total volume expansion is between about 1% and about 90%, between about 5% and about 80%, between about 10% and about 90%, between about 15% and about 85%, or between about 30% and about 80%. Further, in some embodiments, a total volume expansion is time-dependent. For example, in some embodiments, the volume expansion increases with time after combination of the first and second compositions at a first site described herein. Further, in some embodiments, the volume expansion at least partially causes the separation of a first and second tissue layer described herein.

Moreover, the expansion volume of a gel described herein, in some embodiments, can be tuned by altering one or more of the components of a first and/or second composition described herein. For example, in some embodiments, the total expansion volume can be altered based on the identity and/or amount of one or more of a polymerizable material, cross linker, polymerization initiator, and gas foaming agent described herein.

In addition, a method described herein further comprises separating the first tissue layer from a second tissue layer. In some embodiments, the first tissue layer and the second tissue layer are immediately adjacent layers. In other embodiments, the first tissue layer and the second tissue layer are not immediately adjacent layers. Separating a first tissue layer from a second tissue layer, in some embodiments, is facilitated by disposing the first and second compositions at a first site comprising an interfacial region between the first and second tissue layers. Moreover, separating a first tissue layer from a second tissue layer, in some embodiments, comprises forming a gap between the tissue layers. In some embodiments, separating a first tissue layer from a second tissue layer comprises increasing a gap or distance between the tissue layers.

Further, separating a first tissue layer from a second tissue layer, in some embodiments, comprises forming a gap between the tissue layers of at least about 1 mm. In some embodiments, separating a first tissue layer from a second tissue layer comprises forming a gap between the tissue layers of at least about 5 mm or at least about 10 mm. In some embodiments, separating a first tissue layer from a second tissue layer comprises forming a gap between the tissue layers of about 1 mm to about 10 mm, about 3 mm to about 10 mm, about 4 mm to about 10 mm, about 5 mm to about 8 mm, or about 5 mm to about 10 mm.

Moreover, in some embodiments, separation between a first tissue layer and a second tissue layer is at least partially provided by polymerizing a polymerizable material as described herein. For instance, in some embodiments, separation between a first tissue layer and a second tissue layer is provided by forming a gel. In some embodiments, separation between a first tissue layer and a second tissue layer is provided by a gas. In some embodiments, for example, separating a first tissue layer from a second tissue layer comprises providing a gas between the first and second tissue layers. A gas, in some embodiments, is provided by a gas foaming agent of a second composition described herein. A gas foaming agent, in some embodiments, is operable to produce a gas when combined with a first composition described herein. For example, in some embodiments, a gas foaming agent is operable to produce a gas when combined with an acidic first composition. In addition, in some embodiments, the amount of tissue separation can be altered based on the identity and/or amount of a gas foaming agent described herein.

Further, a first tissue layer and/or a second tissue layer described herein, in some embodiments, comprises soft tissue. In some embodiments, a first tissue layer and/or a second tissue layer comprises gastrointestinal (GI) tissue, such as GI mucosal, submucosal, or muscle tissue. Moreover, in some embodiments, neither a first tissue layer nor a second tissue layer comprises hard tissue, such as bone tissue or tooth tissue. In addition, in some embodiments, a first tissue layer and a second tissue layer comprise differing tissues. For instance, in some embodiments, a first tissue layer comprises mucosal or submucosal tissue and a second tissue layer comprises muscle tissue. In some embodiments, a first tissue layer comprises diseased tissue and a second tissue layer comprises healthy tissue. Diseased tissue, in some embodiments, comprises cancerous tissue or a lesion.

In some embodiments, separating a first tissue layer from a second tissue layer comprises elevating the height or lift of a mucosal or submucosal layer. Further, the initial mucosal or submucosal height or lift elevation, in some embodiments, is between about 1 mm and about 10 mm. In some embodiments, the initial elevation is between about 3 mm and about 10 mm, between about 4 mm and about 10 mm, between about 5 mm and about 8 mm, or between about 5 mm and about 10 mm. In some embodiments, the initial elevation is greater than that produced by saline. Further, in some embodiments, the initial elevation can be tuned by altering one or more of the components of a first and/or second composition described herein. For example, in some embodiments, the initial elevation can be altered based on the identity and/or amount of one or more of a polymerizable material, cross linker, and polymerization initiator described herein.

In addition, in some embodiments, a method described herein further comprises maintaining separation of the first and second tissue layers at a desired distance for a therapeutically effective period of time. In some embodiments, for example, a method comprises maintaining a separation of the first and second tissue layers for a time period sufficient to carry out endoscopic resection, including resection of diseased tissue. In some embodiments, a method comprises maintaining at least about 90% or at least about 80% of an initial tissue separation for over 1 hour. In some embodiments, a method comprises maintaining at least about 90% or at least about 80% of the initial tissue separation for a duration of about 1 minute to about 2 hours.

In some embodiments, a method comprises maintaining a tissue separation of at least about 1 mm for at least about 1 hour. In some embodiments, a method comprises maintaining a tissue separation of at least about 5 mm or at least about 10 mm for at least about 1 hour or at least about 2 hours. In some embodiments, a method comprises maintaining a tissue separation of about 1 mm to about 10 mm or about 5 mm to about 10 mm for about 1 minute to about 2 hours. In some embodiments, a method comprises maintaining a tissue separation of about 1 mm to about 10 mm or about 5 mm to about 10 mm for about 3 minutes to about 10 minutes, about 10 minutes to about 2 hours, about 30 minutes to about 90 minutes, about 30 minutes to about 60 minutes, or about 60 minutes to about 90 minutes. Further, in some embodiments, the duration of tissue separation can be tuned by altering one or more of the components of a first and/or second composition described herein. For example, in some embodiments, the duration of tissue separation can be altered based on the identity and/or amount of one or more of a polymerizable material, cross linker, polymerization initiator, and gas foaming agent described herein.

Moreover, in some embodiments, a method described herein further comprises removing at least a portion of a first tissue layer from the body. For example, in some embodiments, a method further comprises removing at least a portion of diseased tissue such as cancerous tissue or potentially cancerous tissue. Moreover, removing at least a portion of a first tissue layer, in some embodiments, comprises electrocauterizing the tissue.

Further, in some embodiments, a method described herein further comprises dispensing a drug into a tissue layer from a composition or gel described herein. For example, in some embodiments, a method described herein further comprises dispensing a drug into tissue remaining after at least a portion of a diseased tissue layer is removed. Dispensing a drug, in some embodiments, can promote healing of remaining tissue and/or additional treatment of a tissue layer. In some embodiments, for instance, dispensing a drug promotes mucosal healing and/or regeneration. Moreover, in some embodiments, dispensing a drug comprises slowly releasing the drug. Slow release of a drug, in some embodiments, provides long-lasting therapeutic effects to one or more tissue layers. For example, in some embodiments, a drug is dispensed over the course of up to 2 weeks. In some embodiments, dispensing a drug comprises quickly releasing an initial amount of the drug followed by slowly releasing the remainder of the drug. Further, the dispensing profile of a drug described herein, in some embodiments, can be controlled by altering one or more of the components of a first and/or second composition described herein. For example, in some embodiments, the dispensing profile can be altered based on the identity and/or amount of one or more of a polymerizable material, cross linker, and polymerization initiator described herein.

In addition, in some embodiments, a method described herein further comprises dispensing an imaging agent into a tissue layer from a composition or gel described herein. Dispensing an imaging agent, in some embodiments, can permit imaging of one or more tissue layers before, during, and/or after tissue separation, resection, and/or treatment.

Moreover, in some embodiments, a method described herein further comprises degrading a polymerizable material and/or a polymerization product of a polymerizable material described herein, such as a gel. Degrading, in some embodiments, comprises biodegrading, including biodegrading in vivo. Biodegrading a polymerizable material and/or a polymerization product of a polymerizable material, in some embodiments, comprises degrading the polymerizable material and/or polymerization product to non-toxic components which can be cleared from the body by ordinary biological processes. In some embodiments, a polymerizable material and/or polymerization product completely or substantially completely degrades over the course of about 4 weeks or less.

In another aspect, a method of separating biological tissue comprises providing a composition comprising a polymerizable material, disposing the composition at a first site beneath a first tissue layer, polymerizing the polymerizable material at the first site, and separating the first tissue layer from a second tissue layer. The composition, in some embodiments, further comprises all components required to polymerize the polymerizable material at the first site, without the need to heat or irradiate the first site. For example, in some embodiments, the composition comprises one or more components of a first composition described hereinabove and one or more components of a second composition described hereinabove. Any components not inconsistent with the objectives of the present invention may be used. Moreover, in some embodiments, the components are selected to achieve a desired polymerization rate such as a slow reaction rate, as described further hereinbelow. In addition, in some embodiments, the method comprises one or more additional steps. For example, in some embodiments, the method further comprises maintaining separation of the first and second tissue layers for a therapeutically effective period of time, as described hereinabove. In some embodiments, the method further comprises removing at least a portion of the first tissue layer from the body, as described hereinabove. In some embodiments, the method further comprises dispensing a drug and/or an imaging agent into a tissue layer from a composition or gel described herein, as described hereinabove. In some embodiments, the method further comprises degrading the polymerizable material and/or a polymerization product of the polymerizable material, such as a gel, as described hereinabove.

Figure 1:
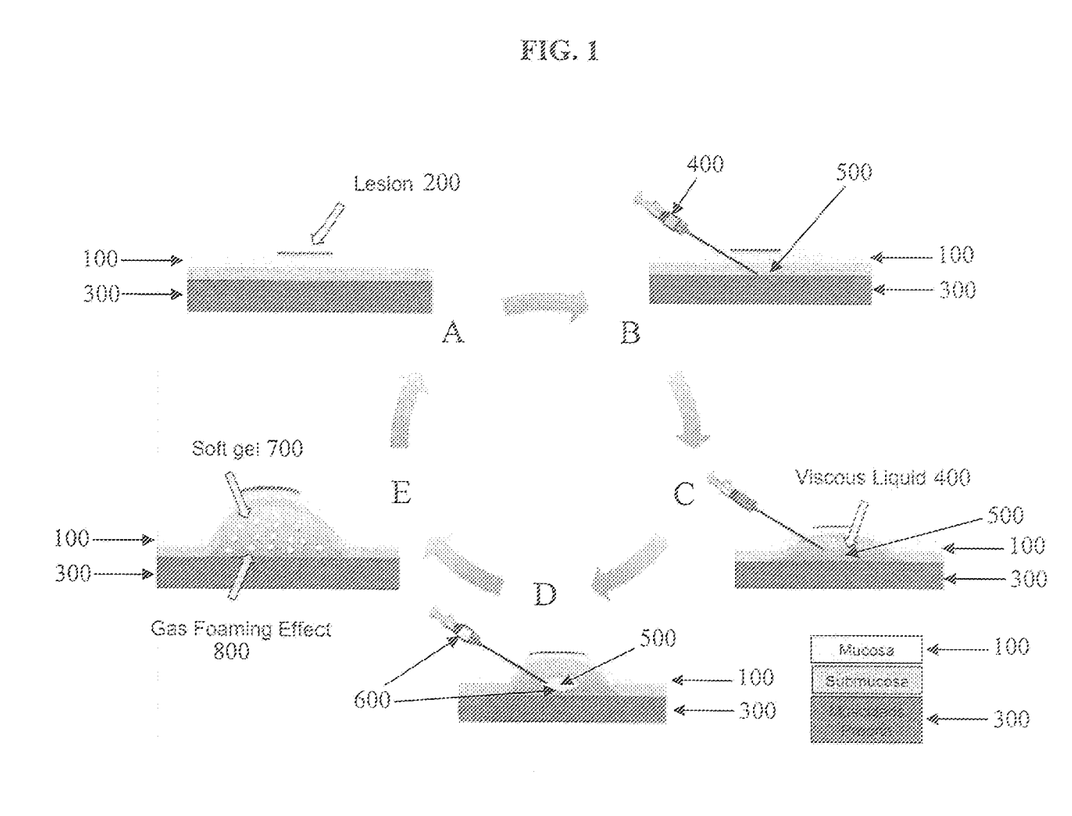
FIG. 1 illustrates a method for separating tissue according to one embodiment described herein.

FIG. 1 illustrates a method for separating tissue according to one embodiment described herein. In the embodiment of FIG. 1, first tissue layer 100 comprises a lesion 200 (FIG. 1A). The lesion 200 is substantially confined to the superficial mucosal and submucosal layers, which are positioned over second tissue layer 300. Second tissue layer 300 comprises healthy muscle tissue. A first composition 400 is disposed at a first site 500 beneath the first tissue layer 100 (FIGS. 1B and 1C), causing separation of the first tissue layer 100 from the second tissue layer 300 (FIG. 1C). In the embodiment of FIG. 1, first composition 400 is an aqueous solution having a viscosity greater than saline. Further, first composition 400 remains a liquid at the first site 500 prior to addition of a second composition 600. When a second composition 600 is disposed at the first site 500 (FIG. 1D), a gel 700 is formed (FIG. 1E). In the embodiment of FIG. 1, second composition 600 comprises an aqueous solution. Formation of the gel 700 increases the separation of the first tissue layer 100 from the second tissue layer 300. In addition, disposing the second composition 600 at the first site 500 produces a gas 800 through reaction of a gas foaming agent (not shown) of the second composition 600 with one or more acid groups of the polymerizable material (not shown) of the first composition 400 (FIG. 1E). Providing a gas 800 results in further separation of the first tissue layer 100 from the second tissue layer 300 (FIG. 1E).

Turning now to specific steps of methods, methods for separating tissue described herein comprise providing a first composition comprising a polymerizable material. Any polymerizable material not inconsistent with the objectives of the present invention may be used. For example, in some embodiments, a polymerizable material is monomeric. In some embodiments, a polymerizable material is oligomeric or polymeric. Moreover, in some embodiments, a polymerizable material comprises one or more olefin moieties, such as a vinyl group. In some embodiments, a polymerizable material comprises one or more carboxyl and/or hydroxyl groups. In some embodiments, a polymerizable material comprises a polymer or oligomer formed from an olefin-containing monomer, such as an unsaturated polyol or polycarboxylic acid. In some embodiments, a polymerizable material comprises a polymer or oligomer formed from a polycarboxylic acid, a polyol, and an olefin-containing monomer. A polycarboxylic acid, in some embodiments, comprises a dicarboxylic acid. In some embodiments, a polycarboxylic acid comprises a tricarboxylic acid. In some embodiments, a polycarboxylic acid comprises citric acid. A polyol, in some embodiments, comprises an alkane diol, such as an α,ω-alkane diol, including a C2-C12 alkane diol. In some embodiments, a polyol comprises a poly(ethylene glycol). Any poly(ethylene glycol) not inconsistent with the objectives of the present invention may be used. In some embodiments, for instance, a poly(ethylene glycol) has a molecular weight between about 100 and about 5000. An olefin-containing monomer, in some embodiments, comprises an olefin moiety and one or more other polymerizable groups, such as one or more alcohol groups, one or more carboxylic acid groups, or one or more anhydride groups. For example, in some embodiments, an olefin-containing monomer comprises an unsaturated polyol or polyacid such as a vinyl-containing diol or a vinyl-containing dicarboxylic acid. In some embodiments, the one or more other polymerizable groups of an olefin-containing monomer are operable to react and form a bond with a hydroxyl group, such as a hydroxyl group of a polyol described herein. In some embodiments, an olefin-containing monomer comprises one or more of fumaric acid, itaconic acid, allylmalonic acid, maleic acid, and maleic anhydride.

In some embodiments, a polymerizable material comprises a polymer or oligomer formed from citric acid, a polyol, and maleic acid. In some embodiments, a polymerizable material comprises poly(ethylene glycol maleate citrate) (PEGMC). In some embodiments, a polymerizable material comprises a polymer or oligomer described in Gyawali et al., "Citric acid-derived in situ crosslinkable biodegradable polymers for cell delivery," *Biomaterials* 2010, 31, 9092-9105; or United States Patent Application Publication No. 2011/0124765, the entireties of which are hereby incorporated by reference.

In some embodiments, a polymerizable material is formed from one or more monomers of Formula (A), one or more monomers of Formula (B) or (B'), and one or more monomers of Formula (C) or Formula (C'):

wherein $R_1$, $R_2$, $R_3$, and $R_4$ are independently —H, methyl, or ethyl,

$R_5$ and $R_6$ are independently —H, —OH, —$OR_7$, methyl, or ethyl, $R_7$ is methyl or ethyl, and n and m are independently integers ranging from 1 to 100.

Further, the monomers of Formula (A), (B), (B'), (C) and (C') can be used in any ratio not inconsistent with the objectives of the present invention. In addition, altering the ratios of monomers can, in some embodiments, alter the reactivity and/or other properties of the polymerizable material formed from the monomers. Moreover, in some embodiments, the reactivity and/or other properties of a polymerizable material can affect one or more of the in situ polymerization, cross linking, gel formation, gel time, gel properties, mucosal lift elevation, and/or mucosal lift duration of a method described herein. In some embodiments, the ratio of monomer (A) to monomer (B) or monomer (B') is between about 1:10 and about 10:1 or between about 1:5 and about 5:1. In some embodiments, the ratio of monomer (A) to monomer (B) or monomer (B') is between about 1:4 and about 4:1. In some embodiments, the ratio is about 1:1. Further, in some embodiments, the ratio of monomer (A) to monomer (C) or monomer (C') is between about 1:10 and about 10:1. In some embodiments, the ratio of monomer (A) to monomer (C) or monomer (C') is about 1:1.

In some embodiments, a polymerizable material comprises a polymer or oligomer of Formula (I):

wherein $R_8$ is $R_9$ is x and y are integers independently ranging from 1 to 100; and z is an integer ranging from 1 to 20.

In some embodiments, a polymerizable material described herein has a molecular weight between about 500 and about 50,000. In some embodiments, a polymerizable material has a molecular weight between about 500 and about 20,000, between about 1000 and about 10,000 or between about 500 and about 5000.

In addition, in some embodiments of methods described herein, a polymerizable material is biodegradable. A biodegradable polymerizable material, in some embodiments, comprises one or more ester bonds. Moreover, in some embodiments, a biodegradable material degrades in vivo to non-toxic components which can be cleared from the body by ordinary biological processes.

Further, in some embodiments, a polymerizable material described herein is biocompatible or cytocompatible. A biocompatible or cytocompatible material, in some embodiments, is non-toxic and does not cause substantial tissue inflammation.

Moreover, in some embodiments, a polymerizable material described herein is water soluble or water dispersible. In some embodiments, for example, a first composition described herein comprises a polymerizable material dissolved or substantially dissolved in an aqueous solution. In other embodiments, a first composition comprises a polymerizable material suspended in an aqueous solution. An aqueous solution, in some embodiments, comprises ultrapure water. In other embodiments, an aqueous solution comprises phosphate buffered saline (PBS).

In addition, a polymerizable material described herein can be present in a first composition in any amount not inconsistent with the objectives of the present invention. For example, in some embodiments, a polymerizable material is present in a first composition in an amount between about 10 weight percent and about 60 weight percent. In some embodiments, a polymerizable material is present in a first composition in an amount between about 10 weight percent and about 50 weight percent, between about 10 weight percent and about 40 weight percent, between about 10 weight percent and about 30 weight percent, between about 20 weight percent and about 60 weight percent, or between about 20 weight percent and about 40 weight percent.

Further, in some embodiments, a first composition comprises one or more species in addition to a polymerizable material. For example, in some embodiments, a first composition further comprises a cross linker. Any cross linker not inconsistent with the objectives of the present invention may be used. In some embodiments, for example, a cross linker comprises one or more olefins or olefinic moieties. In some embodiments, a cross linker comprises an acrylate or polyacrylate, including a diacrylate. In some embodiments, a cross linker comprises one or more of 1,3-butanediol diacrylate, 1,6-hexanediol diacrylate, glycerol 1,3-diglycerolate diacrylate, di(ethylene glycol)diacrylate, poly(ethylene glycol)diacrylate, poly(propylene glycol)diacrylate, and propylene glycol glycerolate diacrylate. In some embodiments, a cross linker comprises a nucleic acid, including DNA or RNA. In some embodiments, a cross linker comprises a "click chemistry" reagent, such as an azide or an alkyne. In some embodiments, a cross linker comprises an ionic cross linker.

In addition, a cross linker described herein can be present in a first composition in any amount not inconsistent with the objectives of the present invention. For example, in some embodiments, a cross linker is present in a first composition in an amount between about 5 weight percent and about 50 weight percent. In some embodiments, a cross linker is present in a first composition in an amount between about 5 weight percent and about 40 weight percent, between about 5 weight percent and about 30 weight percent, between about 10 weight percent and about 40 weight percent, between about 10 weight percent and about 30 weight percent, or between about 20 weight percent and about 40 weight percent.

Moreover, in some embodiments described herein, a first composition further comprises an imaging agent. Any imaging agent not inconsistent with the objectives of the present invention may be used. In some embodiments, for example, an imaging agent comprises a radiopaque material. A radiopaque material, in some embodiments, comprises barium or iodine. In some embodiments, an imaging agent comprises a dye, such as an organic dye. For instance, in some embodiments, an imaging agent comprises methylene blue. In some embodiments, an imaging agent comprises a fluorescent dye. In some embodiments, an imaging agent comprises a fluorescent protein. In some embodiments, an imaging agent comprises a lanthanide species, such as a lanthanide chelate. In some embodiments, an imaging agent comprises a quantum dot, including a II-VI or III-V quantum dot. Moreover, in some embodiments, an imaging agent comprises a luminescent oligomer or polymer, including a luminescent oligomer or polymer comprising an alpha-amino acid such as cysteine. An alpha-amino acid, in some embodiments, is disposed in or chemically bonded to a polymerizable material described herein. For example, in some embodiments, an alpha-amino acid is polymerized or oligomerized with one or more other monomers of a polymerizable material described herein.

An imaging agent described herein can be present in a first composition in any amount not inconsistent with the objectives of the present invention. In some embodiments, for instance, an imaging agent is present in a first composition in an amount between about 0.01 mg/mL and about 100 mg/mL.

In addition, in some embodiments, a first composition further comprises a drug. Any drug not inconsistent with the objectives of the present invention may be used. In some embodiments, for example, a drug comprises a mucosal protective pharmaceutical or an ulcer healing pharmaceutical. In some embodiments, a drug comprises a prostaglandin generation promoter. In some embodiments, a drug comprises a proton-pump inhibitor. In some embodiments, a drug comprises a hemostatic and/or anti-neoplastic composition. In some embodiments, a drug comprises Rebamipide and/or omeprazole.

Moreover, a drug described herein, in some embodiments, is water soluble. In other embodiments, a drug is disposed in a polymeric micelle in the first composition. In some embodiments, a drug described herein is chemically bonded to a polymerizable material described herein, such as through one or more covalent bonds. One or more covalent bonds, in some embodiments, comprise bonds between a hydroxyl or carboxyl group of the polymerizable material and an appropriate functional group on the drug, such as an amine group. In some embodiments, a drug is chemically bonded to a polymerizable material through one or more ionic bonds, electrostatic bonds, or hydrogen bonds.

A drug described herein can be present in a first composition in any amount not inconsistent with the objectives of the present invention. In some embodiments, for instance, a drug is present in a first composition in an amount between about 0.01 mg/mL and about 100 mg/mL. In some embodiments, a drug is present in a first composition in an amount between about 0.1 mg/mL and about 10 mg/mL or between about 0.1 mg/mL and about 1 mg/mL.

Further, in embodiments described herein wherein a first composition comprises a plurality of components, the plurality of components can be present in the first composition in any ratio not inconsistent with the objectives of the present invention. For example, in some embodiments, the ratio of polymerizable material to cross linker is between about 10:1 and about 1:10. In some embodiments, the ratio of polymerizable material to cross linker is between about 10:1 and about 1:1, between about 10:1 and about 5:1, between about 5:1 and about 1:5, between about 5:1 and about 1:2, between about 5:1 and about 1:1, or between about 2:1 and about 1:2. In some embodiments, the ratio of polymerizable material to cross linker is about 1:1.

In addition, a first composition described herein can have any viscosity not inconsistent with the objectives of the present invention. In some embodiments, for instance, a first composition has a viscosity greater than saline solution, such as 0.9% saline solution. In some embodiments, a first composition has a viscosity high enough to minimize migration of the first composition from the injection site over the time scale of a method described herein but low enough to permit injection through an endoscopic needle at an acceptable injection pressure. In some embodiments, a first composition has a viscosity between about 1 centipoise (cP) and about 50 cP at 37° C. In some embodiments, a first composition has a viscosity between about 1 cP and about 20 cP, between about 1 cP and about 10 cP, between about 1.5 cP and about 9 cP, between about 2 cP and about 8 cP, or between about 2 cP and about 5 cP at 37° C. Further, in some embodiments, a first composition exhibits an injection pressure between about 10 psi and about 100 psi when injected at a rate of 20 mL/min using a 10 mL syringe fitted with a 25-gauge needle. In some embodiments, a first composition exhibits an injection pressure between about 20 psi and about 80 psi, between about 20 psi and about 60 psi, between about 20 psi and about 50 psi, or between about 20 psi and about 30 psi.

Methods for separating tissue described herein also comprise providing a second composition comprising a polymerization initiator. Any polymerization initiator not inconsistent with the objectives of the present invention may be used. For example, in some embodiments, a polymerization initiator comprises a free radical initiator. In some embodiments, a polymerization initiator comprises a redox initiator. In some embodiments, a polymerization initiator comprises an oxidizing agent. Further, in some embodiments, a polymerization initiator is water soluble. In some embodiments, a polymerization initiator comprises a halide, persulfate, azo compound, or peroxide. In some embodiments, a polymerization initiator comprises an amine, including a diamine. In some embodiments, a polymerization initiator comprises one or more of ammonium persulfate, potassium persulfate, 4,4'-azobis(4-cyanovaleric acid), and 2,2'-azobis(2-methylpropionamidine)dihydrochloride.

Further, in some embodiments, a second composition described herein comprises a polymerization initiator dissolved or substantially dissolved in an aqueous solution. An aqueous solution, in some embodiments, comprises ultrapure water. In other embodiments, an aqueous solution comprises phosphate buffered saline (PBS).

In addition, a polymerization initiator described herein can be present in a second composition in any amount not inconsistent with the objectives of the present invention. In some embodiments, for instance, a polymerization initiator is present in a second composition in an amount between about 0.1 weight percent and about 3 weight percent. In some embodiments, a polymerization initiator is present in a second composition in an amount between about 0.1 weight percent and about 1 weight percent, or between about 0.1 weight percent and about 0.5 weight percent.

Moreover, in some embodiments of methods described herein, a second composition comprises one or more species in addition to a polymerization initiator. For example, in some embodiments, a second composition further comprises a gas foaming agent. Any gas foaming agent not inconsistent with the objectives of the present invention may be used. For instance, in some embodiments, a gas foaming agent comprises bicarbonate. A gas foaming agent comprising bicarbonate, in some embodiments, can release carbon dioxide gas when combined with a first composition, such as a first composition comprising an acid. Non-limiting examples of gas foaming agents suitable for use in some embodiments described herein include sodium bicarbonate, potassium bicarbonate, and ammonium bicarbonate.

A gas foaming agent described herein can be present in a second composition in any amount not inconsistent with the objectives of the present invention. For example, in some embodiments, a gas foaming agent is present in the second composition in an amount between about 1 weight percent and about 20 weight percent. In some embodiments, a gas foaming agent is present in the second composition in an amount between about 1 weight percent and about 10 weight percent, between about 1 weight percent and about 5 weight percent, or between about 5 weight percent and about 10 weight percent.

In some embodiments, a second composition described herein further comprises a drug and/or imaging agent. A drug and/or imaging agent of a second composition can comprise any drug and/or imaging agent described hereinabove regarding the first composition. Moreover, a drug and/or imaging agent can be present in a second composition in any amount not inconsistent with the objectives of the present invention. For example, in some embodiments, a drug or imaging agent is present in a second composition in an amount between about 0.01 mg/mL and about 100 mg/mL.

Further, a second composition described herein can have any viscosity not inconsistent with the objectives of the present invention. In some embodiments, the viscosity of the second composition is sufficiently low for injection of the second composition through an endoscopic needle. In some embodiments, the viscosity of the second composition is sufficiently high to permit the second composition to remain in the area of the injection site for a time period sufficient to permit cross linking, polymerization, and/or gelling of the polymerizable material of a first composition described herein. In some embodiments, a second composition has a viscosity between about 1 cP and about 5 cP, between about 1 cP and about 3 cP, or between about 1 cP and about 2 cP at 37° C.

In embodiments described herein wherein a second composition comprises a plurality of components, the plurality of components can be present in the second composition in any ratio not inconsistent with the objectives of the present invention. Further, a second composition described herein can be provided in any amount not inconsistent with the objectives of the present invention, including in any suitable ratio compared to the first composition. For example, in some embodiments, the ratio of the first composition to the second composition is between about 10:1 and about 1:10. In some embodiments, the ratio of the first composition to the second composition is between about 5:1 and about 1:5, between about 2:1 and about 1:2, or about 1:1.

Methods described herein also comprise disposing a first composition and a second composition at a first site beneath a first tissue layer. A first or second composition can be disposed at the first site in any manner not inconsistent with the objectives of the present invention. In some embodiments, for instance, a composition is injected at a first site. Moreover, injecting, in some embodiments, comprises injecting with a syringe. In some embodiments, injecting comprises injecting with an endoscopic device, such as an endoscope or endoscopic needle. Further, in some embodiments, a composition such as a first composition is disposed in direct contact with tissue at the first site.

Methods described herein, in some embodiments, also comprise removing at least a portion of a first tissue layer from the body. At least a portion of a first tissue layer can be removed in any manner not inconsistent with the objectives of the present invention. In some embodiments, for example, removing is carried out endoscopically, including with an endoscope or other endoscopic device.

Methods described herein, in some embodiments, further comprise dispensing a drug and/or an imaging agent into a tissue layer from a composition or gel described herein. Dispensing a drug and/or imaging agent can be carried out in any manner not inconsistent with the objectives of the present invention. In some embodiments, for instance, dispensing comprises permitting slow release of the drug and/or imaging agent via diffusion of the drug and/or imaging agent out of the composition or gel. In some embodiments, dispensing comprises releasing via degradation of the composition or gel, such as biodegradation of the composition or gel.

II. Systems for Use in Tissue Separation Applications

In another aspect, systems for use in tissue separation applications are described herein. Tissue separation applications, in some embodiments, include applications requiring the separation of unhealthy tissue such as tumor tissue from healthy tissue. For example, in some embodiments, tissue separation applications include endoscopic resection applications such as EMR and ESD, including injection-assisted EMR and ESD. In some embodiments, tissue separation applications include separation of the prostate from the rectum during prostate radiation therapy.

In some embodiments, a system for use in tissue separation applications comprises a first composition comprising a polymerizable material, a second composition comprising a polymerization initiator, and an endoscopic device. In some embodiments, the first composition further comprises a cross linker. In some embodiments, the second composition further comprises a gas foaming agent. In some embodiments, the first composition and/or the second composition further comprises a drug and/or an imaging agent.

Turning now to specific components of systems, systems for use in tissue separation applications described herein comprise a first composition comprising a polymerizable material. Any polymerizable material not inconsistent with the objectives of the present invention may be used. In some embodiments, a polymerizable material comprises a polymerizable material described hereinabove in Section I.

Further, in some embodiments, a first composition described herein comprises one or more components in addition to a polymerizable material. In some embodiments, for instance, a first composition further comprises a cross linker. Any cross linker not inconsistent with the objectives of the present invention may be used. In some embodiments, a cross linker comprises any cross linker described hereinabove in Section I. In some embodiments, a first composition further comprises a drug. Any drug not inconsistent with the objectives of the present invention may be used. In some embodiments, a drug comprises any drug described hereinabove in Section I. In some embodiments, a first composition described herein further comprises an imaging agent. Any imaging agent not inconsistent with the objectives of the present invention may be used. In some embodiments, an imaging agent comprises any imaging agent described hereinabove in Section I.

Systems described herein also comprise a second composition comprising a polymerization initiator. Any polymerization initiator not inconsistent with the objectives of the present invention may be used. In some embodiments, a polymerization initiator comprises any polymerization initiator described hereinabove in Section I.

Moreover, in some embodiments, a second composition described herein comprises one or more components in addition to a polymerization initiator. For example, in some embodiments, a second composition described herein further comprises a drug. Any drug not inconsistent with the objectives of the present invention may be used. In some embodiments, a drug comprises any drug described hereinabove in Section I. In some embodiments, a second composition described herein further comprises an imaging agent. Any imaging agent not inconsistent with the objectives of the present invention may be used. In some embodiments, an imaging agent comprises any imaging agent described hereinabove in Section I.

Systems described herein also comprise an endoscopic device. Any endoscopic device not inconsistent with the objectives of the present invention may be used. In some embodiments, an endoscopic device comprises an endoscope. In some embodiments, an endoscopic device comprises an endoscopic needle. In some embodiments, an endoscopic device comprises a camera or lens.

III. Methods for Displacing Soft Biological Tissue

In another aspect, methods for displacing soft biological tissue are described herein. In some embodiments, a method for displacing soft tissue comprises providing a first composition comprising a polymerizable material, providing a second composition comprising a polymerization initiator, disposing the first composition at a first site within a first soft tissue, disposing the second composition at the first site, polymerizing the polymerizable material at the first site, and displacing the first soft tissue. Displacing a first soft tissue, in some embodiments, comprises reducing wrinkles, such as wrinkles on the skin. In some embodiments, displacing a first soft tissue comprises increasing the total volume of a tissue or body part, such as a lip. Moreover, in some embodiments, displacing a first soft tissue comprises displacing the tissue by an amount and for a duration described hereinabove in Section I regarding the separation of tissue layers.

Turning now to specific steps of methods, methods for displacing biological tissue described herein comprise providing a first composition comprising a polymerizable material and a second composition comprising a polymerization initiator. The first composition and second composition can comprise any first composition and second composition described hereinabove in Section I, including any polymerizable material and polymerization initiator described hereinabove in Section I. Similarly, the first and second compositions can be disposed at a first site within a first soft tissue in any manner not inconsistent with the objectives of the present invention, including in a manner described hereinabove in Section I. Further, the first soft tissue can comprise any soft tissue not inconsistent with the objectives of the present invention. In some embodiments, for instance, the first soft tissue comprises skin or lip tissue. In some embodiments, the first soft tissue comprises tissue beneath the skin.

IV. Systems for Use in Tissue Displacement Applications

In another aspect, systems for use in tissue displacement applications are described herein. Tissue displacement applications, in some embodiments, include cosmetics applications such as anti-wrinkle applications and lip-plumping applications. In some embodiments, a system for use in tissue displacement applications comprises a first composition comprising a polymerizable material, a second composition comprising a polymerization initiator, and an injection device.

Turning now to specific components of systems, system for use in tissue displacement applications described herein comprise a first composition comprising a polymerizable material and a second composition comprising a polymerization initiator. The first composition and second composition can comprise any first composition and second composition described hereinabove in Section I, including any polymerizable material and polymerization initiator described hereinabove in Section I. In addition, the injection device of a system described herein can comprise any injection device not inconsistent with the objectives of the present invention. In some embodiments, for example, the injection device comprises a syringe.

Some embodiments described herein are further illustrated in the following non-limiting examples.

EXAMPLE 1

PEGMC

A polymerizable material suitable for use in some embodiments described herein was prepared as follows. Citric acid (0.4 mol, Sigma Aldrich), maleic anhydride (0.6 mol, Sigma Aldrich), and poly(ethylene glycol) (molecular weight 200, 1.0 mol, Sigma Aldrich) were added to a 250-mL round bottom flask equipped with a magnetic stir bar. The mixture was stirred at 300 rpm for 10 minutes at 160° C. under a continuous flow of nitrogen to melt the solids. The temperature was then reduced to 140° C. and stirring was continued for another 2 hours. The pressure inside the flask was then reduced to 50 mTorr for an additional 2 hours. The resulting product was then dissolved in ultrapure water (Millipore, Billerica, Mass.) and purified using a dialysis membrane (500 MW cutoff, Cole-Parmer, Vernon Hills, Ill.). The resulting purified material was then collected and lyophilized to produce a purified PEGMC material.

EXAMPLE 2

First Composition

A first composition suitable for use in some embodiments described herein was prepared as follows. The purified PEGMC material of Example 1 (0.2 g/mL water), poly(ethylene glycol)diacrylate (PEGDA, 700 MW, 0.16 g/mL water, Sigma Aldrich), and tetramethylethylenediamine (TEMED, 6 μL/mL water, Sigma Aldrich) were dissolved in ultrapure water.

The viscosity of the composition was measured using a Brookfield DV-II Cone Plate Viscometer (Brookfield, Middleboro, Mass.). A 1-mL sample of the composition was placed between a 1.565° cone spindle and plate of the viscometer, and the viscosity was measured at 37° C. at 12 rpm.

Figure 2:
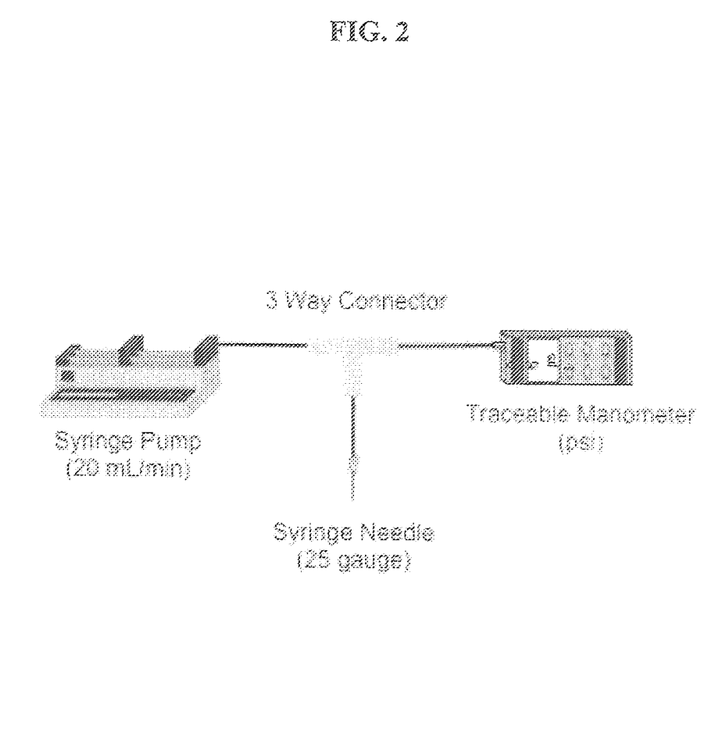
FIG. 2 illustrates the experimental set up for a test procedure used to measure the injection pressure of a composition according to one embodiment described herein.

The maximum injection pressure developed during injection of this composition was measured as follows. A 5-mL sample of the composition was loaded into a 10-mL syringe. The syringe was then loaded onto a syringe pump (KD Scientific Model 200, Holliston, Mass.). Next, the syringe, a digital traceable manometer (Cole-Parmer, Vernon Hills, Ill.), and a 25-gauge, three-foot sclerotherapy needle (US Endoscopy, Mentor, Ohio) were connected to a three-way luer lock stopcock (Qosina, Edgewood, N.Y.) as illustrated in FIG. 2. The injection rate of the syringe pump was set at 20 mL/minute and injection was begun. The maximum pressure value (in psi) was recorded at the time when a steady force of embolus of the syringe produced a fluid jet of stable radius from the tip of the sclerotherapy needle.

EXAMPLE 3

Second Composition

A second composition suitable for use in some embodiments described herein was prepared as follows. Ammonium persulfate (APS) was dissolved in ultrapure water at 0.25 weight percent. In addition, in some embodiments, 5 weight percent sodium bicarbonate was also dissolved in the ultrapure water, providing a second composition comprising both a polymerization initiator (APS) and a gas foaming agent (sodium bicarbonate).

EXAMPLE 4

Gels

A series of gels comprising a cross linked polymerizable material according to some embodiments described herein was formed as follows. A desired amount of the first composition of Example 2 and a desired amount of the second composition of Example 3 were combined in a 2:1 ratio by volume and allowed to mix by diffusion for various times.

Rheological properties of the gels are determined using multiwave rheology experiments applying multiple frequencies simultaneously in oscillatory experiments with time. In particular, the first and second compositions are combined and then immediately transferred to the parallel plate of a rheometer (TA Instrument, ARES-G2, 25 mm plates with a 1.9 mm gap at 37° C.). An oscillatory small strain γ(t) was imposed on the sample:

$$\gamma = \sum_{i=1}^{M} \gamma_i \sin(\omega_i t)$$

where m is the number of the superimposed harmonics, and $\gamma_i$ and $\omega_i$ denote the amplitude and the frequency of the $i^{th}$ harmonic, respectively. The frequencies of the harmonics are $\omega_n = n\omega_f$ with the fundamental frequency $\omega_f$. Further, $\omega_f = 10$ rad/s (n=1, 5, 10) and $\gamma_i = 2\%$. Data collection is started immediately after the sample is loaded and continues for 1000 s. The gel point is identified as the cross-over of the viscous and elastic moduli. Frequency sweep experiments from 0.1 to 100 rad/s are conducted on samples. The strain amplitude in frequency sweep measurements is 10% to remain within the region of viscoelasticity. Viscoelastic properties are characterized by the complex shear modulus:

$$G^* = G' + iG''$$

and complex shear viscosity:

$$\eta^* = G^*/i\omega$$

Figure 3:
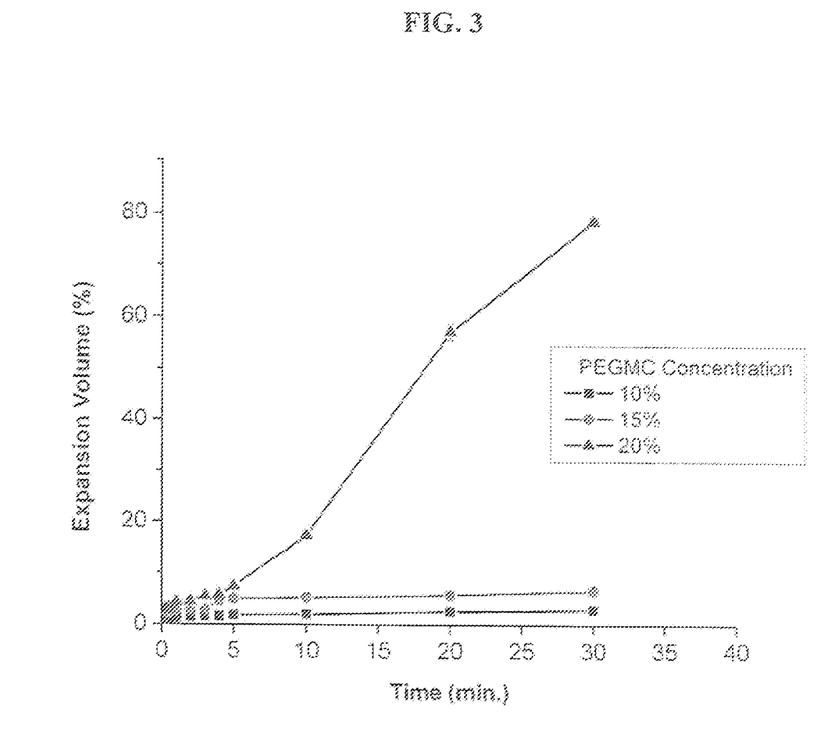
FIG. 3 is a graph showing the total volume expansion associated with the formation of a series of gels provided according to some embodiments of methods described herein.

To determine the overall expansion volumes caused by the formation of the gels, 500 μL of the first composition and 250 μL of the second composition were combined in a 3 mL glass vial and permitted to mix by diffusion. Photographic images were recorded at 0, 0.25, 0.50, 1, 2, 3, 4, 5, 10, 20 and 30 minutes after combination. The expansion volume at time t was determined using Image J Analysis Software and the following equation:

$$\text{Expansion volume (\%)} = 100 \times (V_t - V_0)/V_0,$$

where $V_t$ is the total volume at time t and $V_0$ is the initial total volume. FIG. 3 illustrates the results for a series of gels formed from a series of first compositions having differing concentrations of PEGMC (10 weight percent, 15 weight percent, and 20 weight percent).

The mechanical properties of gels were determined as follows. Mechanical tests were carried out on cylindrical gel samples in an unconfined state 3 mm in diameter and 10 mm in height using an MTS Insight II mechanical tester fitted with a 10 N load cell (MTS, Eden Prairie, Minn.). The load (N) versus compression (%) was recorded using Testworks 4 Software at a crosshead speed of 1 mm/minute at various strain levels. The stress at 50% strain (compressive peak stress) was recorded along with the initial modulus (0-10% strain). Specifically, the initial modulus was calculated from the initial (0-10% strain) slope of the compressive stress vs. strain curve.

The electrical properties of gels are determined as follows. Electrical impedance is measured with a potentiostat electroimpedance spectrometer (Gamry Instruments, Pennsylvania) and insulation tipped knife (Olympus Optical, Tokyo, Japan) using 0.01 N KCl as a reference solution. Material resistance is calculated from the following equation:

$$\rho = 1/\sigma = R_S/K_{cell},$$

where $\rho$ is resistance (Ω cm), $\sigma$ is the conductivity (mS/cm), $R_S$ is electrical impedance (Ω), and $K_{cell}$ is the cell constant.

EXAMPLE 5

Dispensing a Drug

Figure 4:
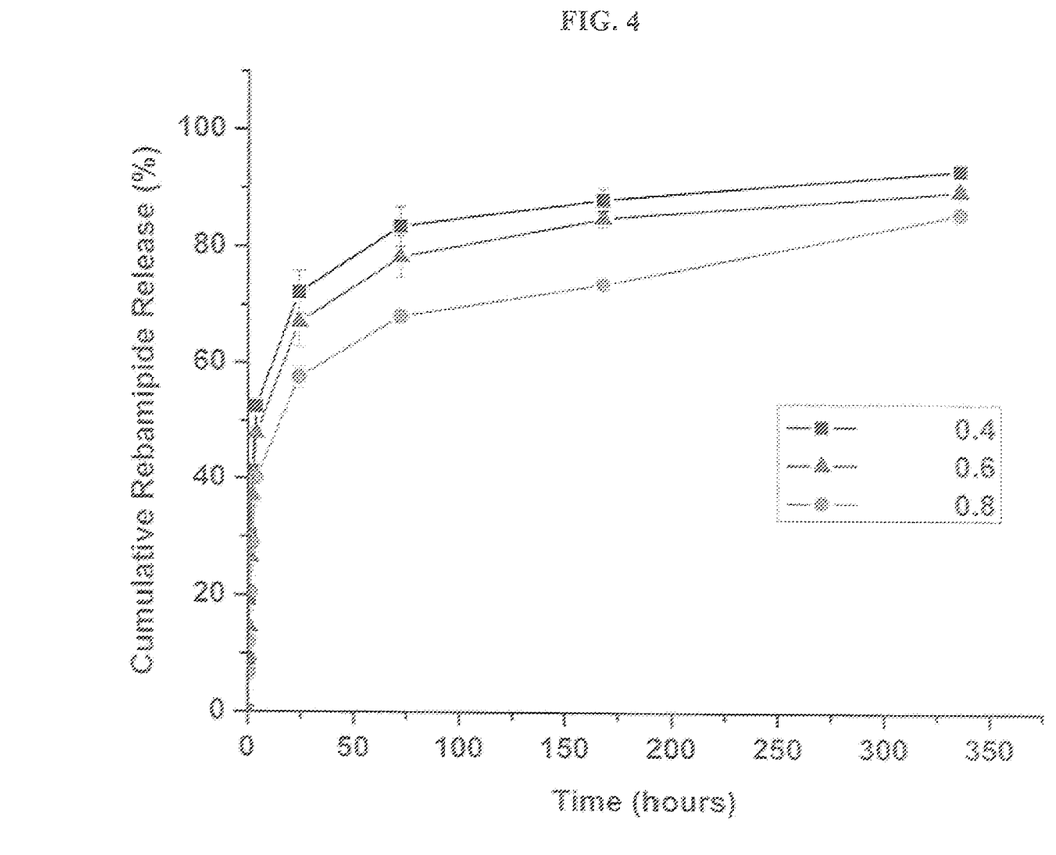
FIG. 4 illustrates the drug delivery profile associated with a series of gels provided according to some embodiments of methods described herein.

The release profile of a drug from a series of gels formed according to some embodiments described herein was determined as follows. Rebamipide (1 mM) was mixed with a series of first compositions produced according to Example 2. The series of first compositions included PEGMC polymerizable materials produced with citric acid to maleic anhydride monomer ratios of 0.4, 0.6, and 0.8. The drug-loaded first compositions were mixed with a series of second compositions produced according to Example 3 to provide a series of gels comprising Rebamipide. The drug-loaded gels were placed in glass vials and allowed to incubate in phosphate buffered saline (37° C., pH 7.4) for 2 weeks. Aliquots (0.2 mL) were taken from the supernatant of each vial at various intervals, and the amount of Rebamipide present in the supernatant was determined by high performance liquid chromatography (HPLC, Waters, Milford, Mass.). FIG. 4 illustrates the results.

EXAMPLE 6

Ex Vivo Studies

Figure 5:
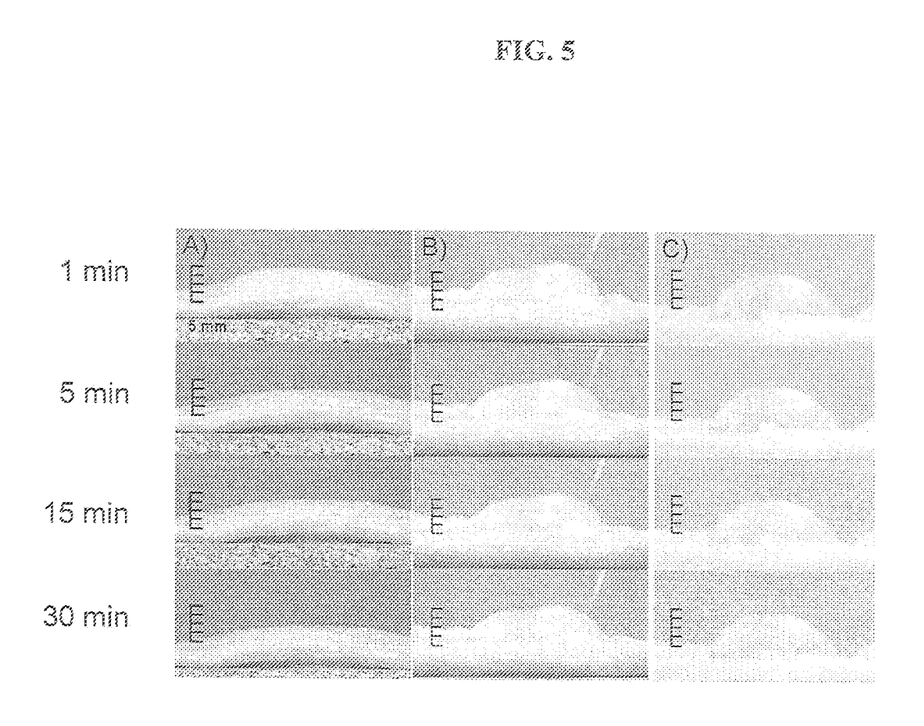
FIG. 5 is a series of photographs of the mucosal elevation provided by one embodiment of a method described herein compared to other methods.
Figure 6:
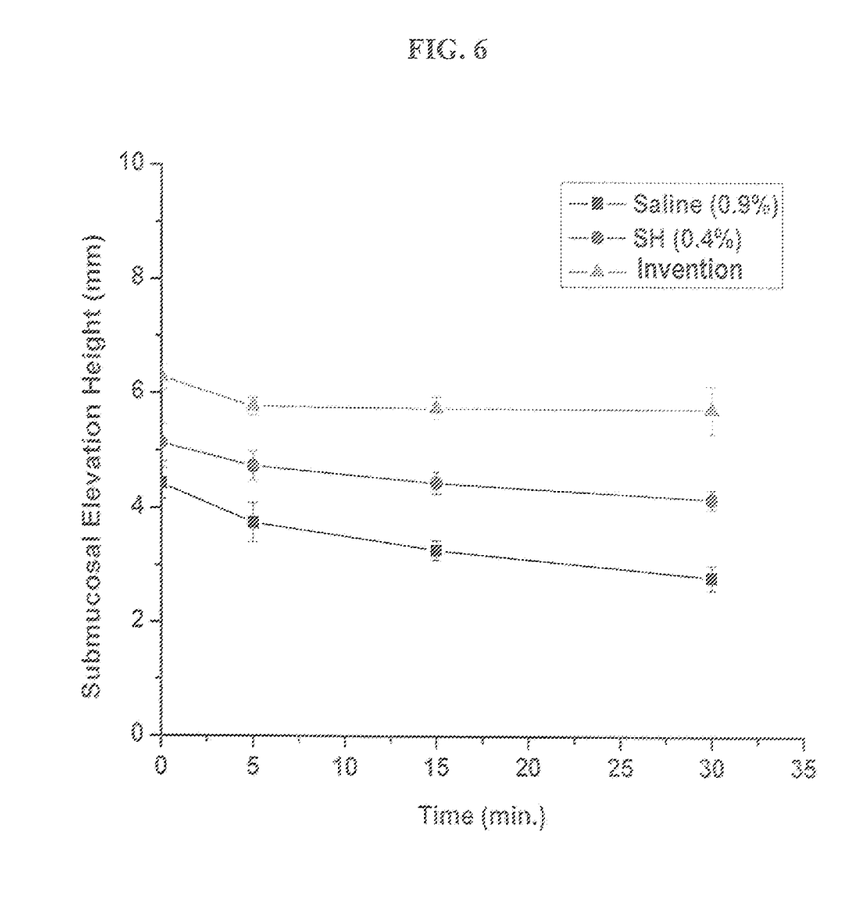
FIG. 6 is a graph illustrating mucosal elevation height as a function of time for the methods of FIG. 5.
Figure 7:
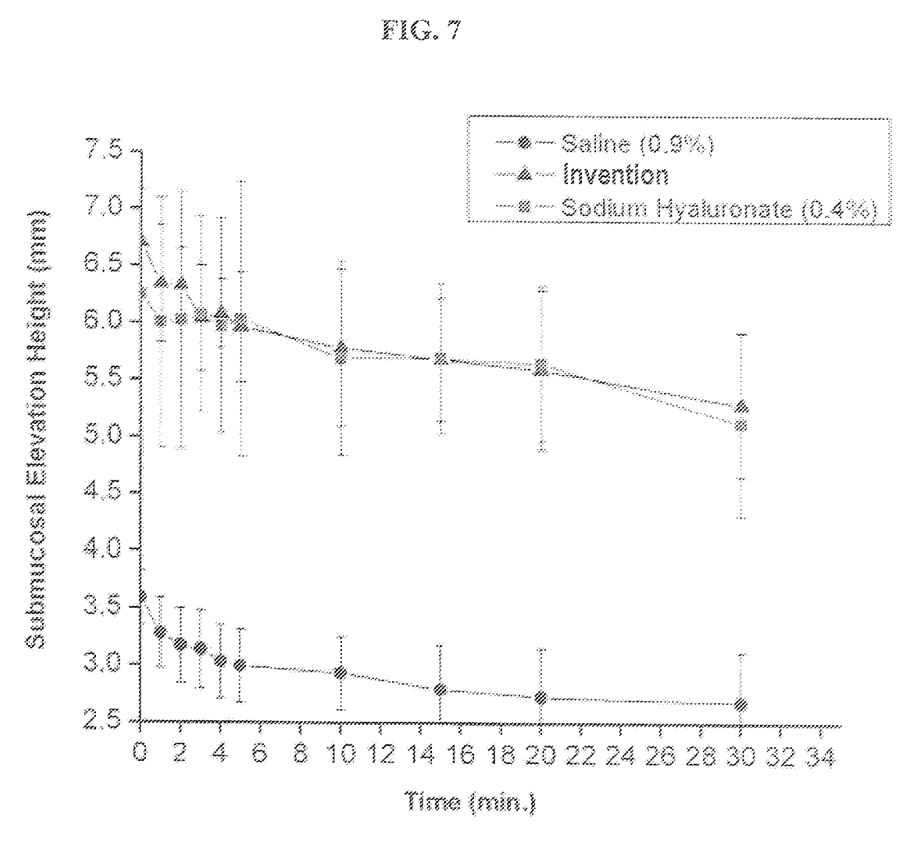
FIG. 7 is a graph illustrating mucosal elevation height as a function of time provided by one embodiment of a method described herein compared to other methods.

Methods of separating tissue according to some embodiments described herein were carried out as follows. Biological tissues were separated ex vivo. The upper thirds of porcine stomachs were used for ex vivo studies due to their resemblance to the human stomach in thickness and histology. Porcine stomach samples were obtained immediately after sacrifice (Columbia Packing, Dallas, Tex.). Each porcine stomach specimen was cut into 5 cm×5 cm pieces and fixed onto a flat corkboard using steel pins. Using a 2.5 mL syringe equipped with a 25-gauge needle, 1 mL of a first composition produced according to Example 2 and 1 mL of a second composition produced according to Example 3 were injected tangentially into the submucosa of the specimens through the mucosal surface. Each of the first and second compositions also contained methylene blue (0.5 mL methylene blue/10 mL composition) for visualization. Photographs of the mucosal elevation were recorded at 0, 1, 2, 3, 4, 5, 10, 15, 20 and 30 minutes immediately following injection. Mucosal elevation heights were determined quantitatively from the photographs using Image J Analysis Software. All injections were performed within 1 hour after the animals' death, and all tests were performed at a constant temperature of 37° C. For comparison, aqueous solutions of saline (0.9%) and sodium hyaluronate (SH, 0.4%) were also injected into porcine stomach specimens as described above. FIG. 5 shows a series of photographs of the mucosal elevation heights for injections using (A) saline, (B) SH, and (C) first and second compositions described herein at 1, 5, 15, and 30 minutes after injection. The data of FIG. 5C was produced using a first composition comprising 30 weight percent PEGMC. The scale bars are 5 mm. All the submucosal cushions created according to a method described herein were more durable than those created with saline or SH. FIG. 6 shows a plot of the mucosal elevation height as a function of time for the injections of FIG. 5. FIG. 7 shows a plot of the mucosal elevation height as a function of time for injections of saline, SH, and first and second compositions described herein, wherein the first composition included 20 weight percent PEGMC and the second composition included sodium bicarbonate.

EXAMPLE 7

In Vivo Studies

Methods of separating tissue according to some embodiments described herein were carried out as follows. Four in vivo EMR procedures were performed using a live porcine stomach model. Veterinary care for the animal subjects was provided by the animal lab at the University of Mississippi Medical Center (UMMC) and maintained under the guidelines of the UMMC Institutional Animal Care and Use Committee according to current NIH guidelines. All surgical manipulations were performed under anesthesia using sterile technique. All of the guidelines as outlined by the American Association for the Accreditation of Laboratory Animal Care were followed to ensure that discomfort, distress, pain, and injury were limited to that which was unavoidable in the conduct of scientifically sound research. All pigs were euthanized by administration of a lethal dose of sodium pentobarbital as per recommendations of the American Veterinary Medical Association.

First and second compositions produced according to Examples 2 and 3, respectively, were injected using the same

25-gauge catheter injection needle. The first composition was easily injected and was able to create an adequate submucosal cushion. The second composition was injected into the same injection site without any clogging inside the delivery tool. Five minutes following injection of the second composition, an "en bloc" resection of the elevated mucosa was performed with a hook-knife and polypectomy snare and recorded with endoscopic photographs. The en bloc resection of the elevated mucosa revealed a soft biodegradable gel underneath the mucosa, providing protection for the underlying muscle layer from electrocautery damage. The presence of the gel did not complicate the resection procedure or require any changes to the electrocautery settings.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method for separating tissue comprising:
providing a first composition comprising a polymerizable material;
providing a second composition comprising a polymerization initiator;
disposing the first composition at a first site beneath a first soft tissue layer, the first site comprising an interfacial region between the first soft tissue layer and an adjacent second soft tissue layer;
disposing the second composition at the first site; and
polymerizing the polymerizable material at the first site,
thereby separating the first tissue layer from the second tissue layer, the separation of the first and second tissue layers being at least partially caused by the polymerization of the polymerizable material at the first site.

2. The method of claim 1, wherein the polymerizable material is formed from one or more monomers of Formula (A), one or more monomers of Formula (B) or (B'), and one or more monomers of Formula (C) or Formula (C'):

wherein $R_1$, $R_2$, $R_3$, and $R_4$ are independently —H, methyl, or ethyl,
$R_5$ and $R_6$ are independently —H, —OH, —OR$_7$, methyl, or ethyl,
$R_7$ is methyl or ethyl, and
n and m are independently integers ranging from 1 to 20.

3. The method of claim 1, wherein the polymerizable material comprises a polymer or oligomer of Formula (I):

wherein $R_8$ is $R_9$ is x and y are integers independently ranging from 1 to 100; and
z is an integer ranging from 1 to 20.

4. The method of claim 1, wherein the first composition further comprises a cross linker.

5. The method of claim 4, wherein the cross linker comprises an acrylate or polyacrylate.

6. The method of claim 1, wherein the first composition further comprises a drug.

7. The method of claim 1, wherein the polymerization initiator comprises a free radical initiator or redox initiator.

8. The method of claim 1, wherein the second composition further comprises a gas foaming agent.

9. The method of claim 8, wherein the gas foaming agent comprises bicarbonate.

10. The method of claim 1, wherein polymerizing the polymerizable material comprises forming a gel.

11. The method of claim 10, wherein the gel has a gel setting time between about 1 minute and about 10 minutes.

12. The method of claim 1, wherein separating the first tissue layer from the second tissue layer comprises providing a gas between the first and second tissue layers and the separation of the first and second tissue layers is at least partially caused by the presence of the gas.

13. The method of claim 1 further comprising maintaining at least about 80% of an initial tissue separation distance of the first and second tissue layers for over 1 hour.

14. The method of claim 1 further comprising removing at least a portion of the first tissue layer from the body following the polymerization of the polymerizable material at the first site.

15. The method of claim 1 further comprising dispensing a drug into a tissue layer from the first or second composition.

16. The method of claim 1 further comprising biodegrading the polymerizable material and/or a polymerization product formed from the polymerizable material.

17. The method of claim 16, wherein the polymerizable material and/or polymerization product formed from the polymerizable material completely degrades in vivo over the course of about 4 weeks or less.

18. The method of claim 1, wherein separating the first tissue layer from the second tissue layer comprises forming a gap between the tissue layers of about 1 mm to about 10 mm.

19. A method for separating tissue comprising:

providing a composition comprising a polymerizable material;

disposing the composition at a first site beneath a first soft tissue layer, the first site comprising an interfacial region between the first tissue layer and an adjacent second soft tissue layer; and polymerizing the polymerizable material at the first site, thereby separating the first tissue layer from the second tissue layer, the separation of the first and second tissue layers being at least partially caused by the polymerization of the polymerizable material at the first site.

* * * * *